United States Patent [19]
Beech, Jr. et al.

[11] Patent Number: 5,986,148
[45] Date of Patent: Nov. 16, 1999

[54] DI-ISOPROPYL ETHER SYNTHESIS AND DRY PRODUCT RECOVERY

[75] Inventors: James H. Beech, Jr., Wilmington, Del.; Douglas Miller, Yardley, Pa.; Jorge Luis Soto, Cranbury, N.J.; James A. Stoos, Beaumont, Tex.; Albert H. Wu, Medford, N.J.

[73] Assignee: Mobil Oil Corporation, Fairfax, Va.

[21] Appl. No.: 08/101,111

[22] Filed: Aug. 2, 1993

[51] Int. Cl.⁶ .................................................. C07C 41/00
[52] U.S. Cl. ........................................... 568/694; 568/695
[58] Field of Search ..................... 568/694, 695

[56] References Cited

U.S. PATENT DOCUMENTS

| | | | |
|---|---|---|---|
| 4,042,633 | 8/1977 | Woods | 260/614 |
| 4,182,914 | 1/1980 | Imaizumi | 568/697 |
| 4,666,563 | 5/1987 | Berg et al. | 203/56 |
| 4,857,664 | 8/1989 | Huang et al. | 568/695 |
| 4,906,787 | 3/1990 | Huang et al. | 568/697 |
| 5,113,024 | 5/1992 | Narandi et al. | 568/694 |
| 5,138,102 | 8/1992 | Beech, Jr. et al. | 568/695 |
| 5,154,801 | 10/1992 | Harandi et al. | 203/43 |
| 5,162,591 | 11/1992 | Beech et al. | 568/695 |

*Primary Examiner*—Johann Richter
*Assistant Examiner*—Joseph Murray
*Attorney, Agent, or Firm*—Malcolm D. Keen

[57] ABSTRACT

An improved process for production of diisopropyl ether by conversion of hydrocarbon feedstock containing propene, propane and $C_2$— light gas components. The overall process steps include, (optionally) prefractionating fresh feedstock containing propene, propane and $C_2$— light gas components to provide a reactor feedstream rich in propene; contacting the feedstock and water in a catalytic reactor with acidic catalyst under olefin hydration and etherification conditions; and recovering from the catalytic reactor a liquid reactor effluent stream containing diisopropyl ether, isopropanol, water, unreacted propene, propane, oligomer and $C_2$— light gas components. DIPE product containing $C_6+$ oligomer is recovered by separating the liquid effluent stream in a stripper column, and extracting the DIPE-rich liquid with water. An improved separation process is employed for removing water to provide DIPE liquid product substantially free of water.

4 Claims, 3 Drawing Sheets

DI-ISOPROPYL ETHER SYNTHESIS AND DRY PRODUCT RECOVERY

BACKGROUND OF THE INVENTION

This invention relates to olefin hydration, especially for production of di-isopropyl ether (DIPE) from $C_3+$ olefinic feedstock. Particularly, the invention relates to a novel technique for recovering dry DIPE product from reactor effluent.

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_3+$aliphatic stream rich in propene and propane. Feedstocks of particular interest are light hydrocarbon streams rich in propene, which are often accompanied by significant amounts of propane, ethene, ethane and other light gases.

Catalytic hydration of olefins to provide alcohols and ethers is established technology for production of the IPA and DIPE and is of significant commercial importance. Olefin hydration employing large pore zeolite (i.e. 7+Angstroms) or medium pore (5–7 Å) catalyst is a known synthesis method. Recently, processes for the direct hydration of olefins to provide alcohols and ethers using porous shape selective metallosilicate zeolite catalyst, such as zeolite Beta have been disclosed in U.S. Pat. No. 4,857,664 (Huang et al.), U.S. Pat. No. 4,886,918 (Sorensen et al), U.S. Pat. Nos. 5,138,102 and 5,162,591 (Beech et al), incorporated herein by reference. Prior processes have attempted to provide a dry DIPE product by various recovery techniques.

It is a main object of this invention to provide an improved process for olefin hydration in a more economical manner and with improved yields of dry ether product. It is a further object to provide novel product recovery techniques for use in DIPE reactor systems.

SUMMARY OF THE INVENTION

A novel process has been discovered for production of ether/alcohol from lower olefins. In the preferred embodiments a process is provided for production of diisopropyl ether by conversion of hydrocarbon feedstock containing propene, propane and $C_2-$ light gas components, including the steps of:

- (optionally) prefractionating fresh feedstock containing propene and other $C_3-$ light gas components to provide a reactor feedstream rich in propene;
- contacting the feedstock and water in a catalytic reactor with acidic catalyst under olefin hydration and etherification reaction conditions, wherein the catalyst comprises porous zeolite having a pore size of 5–8 Angstroms, and reaction temperature is maintained at 100 to 250° C.;
- recovering from the catalytic reactor a liquid reactor effluent stream containing 0.5–10 wt % water, 20–60 wt % propene, 20–30 wt % di-isopropyl ether, 10–15 wt % isopropanol, at least 5 wt % total propane, 0 to 20 wt % oligomer, and 0.1 to 10 wt % $C_2-$ components;
- separating the liquid reactor effluent stream in a vertical stripper column;
- recovering propene and $C_3-$ light gas components from the stripper column;
- recovering from the stripper column an ether-rich liquid stream containing oligomer and isopropanol;
- extracting the ether-rich liquid stream with water to remove isopropanol-rich aqueous extract and recover a wet liquid product stream consisting essentially of di-isopropyl ether, oligomer and at least 0.2 wt % water;
- distilling said wet liquid product stream to recover a major amount of water from the wet liquid product stream along with residual $C_3$ hydrocarbons and to recover a dry bottom ether product stream containing less than 0.1 wt % water and at least 3 wt % oligomer.

For feedstocks rich in propane and/or $C_4+$ components, fresh feedstock is prefractionated to provide a reactor feedstream rich in propene; and the $C_3$ recycle stream may be prefractionated economically with fresh feedstock.

These and other advantages and features of the invention will be seen in the description and drawings.

DETAILED DESCRIPTION OF THE INVENTION

The preferred embodiments of the invention are described with reference to refinery grade propene feedstocks and zeolite catalysts. Metric units and parts by weight are employed unless otherwise indicated.

The olefins hydration and etherification process employs the reaction of propylene with water catalyzed by strong acid to form isopropanol. Reaction may be allowed to continue in the hydration zone to form di-isopropyl ether. The operating conditions of the olefin hydration and etherification reaction step include a temperature of about 50 to 450° C., preferably from 100 to 250° C. and most preferably from 120 to 220° C. The total pressure is about 700 to 24000 kPa (100 to about 3500 psi, preferably 500–2000 psi). Water to olefin reactant concentrations are maintained at mole ratio of about 0.1 to 30, preferably 0.1 to 5.

The preferred catalytic methods for making DIPE employ porous solid acid catalysts, such as zeolites Beta, Y, ZSM-35 and/or MCM-22 aluminosilicate. The preferred hydration/etherification catalyst comprises acidic, shape selective porous zeolite having a pore size of about 5–8 Angstroms, such as aluminosilicate zeolite Beta. Also, MCM-22, having pores similar to zeolite Beta and ZSM-5, is known for etherification catalysis, as disclosed by Marler et al. in U.S. Pat. No. 5,105,023.

DIPE etherification conditions may vary widely in choice of temperature, pressure and reaction time. The preferred method reacts propene with water in an adiabatic downflow reactor containing a fixed bed of catalyst, such as zeolite Beta, at 100 to 250° C. and pressure of at least 4000 kPa. However, it is understood that the unit operations described herein can be conducted with any number of specific process steps within the skill of the art.

The olefin hydration and etherification reaction step is carried out in liquid phase or supercritical dense phase in continuous manner using a fixed bed flow reactor. Weight hourly space velocity, based on catalyst weight is maintained in the range of 0.1 to 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature, phase behavior and flow parameters. It is ordinarily desirable to recover any unreacted olefin and recycle it to the reactor. Unconverted isopropanol recovered from the final reactor effluent may also be recycled advantageously for further conversion to ether.

Figure 1:
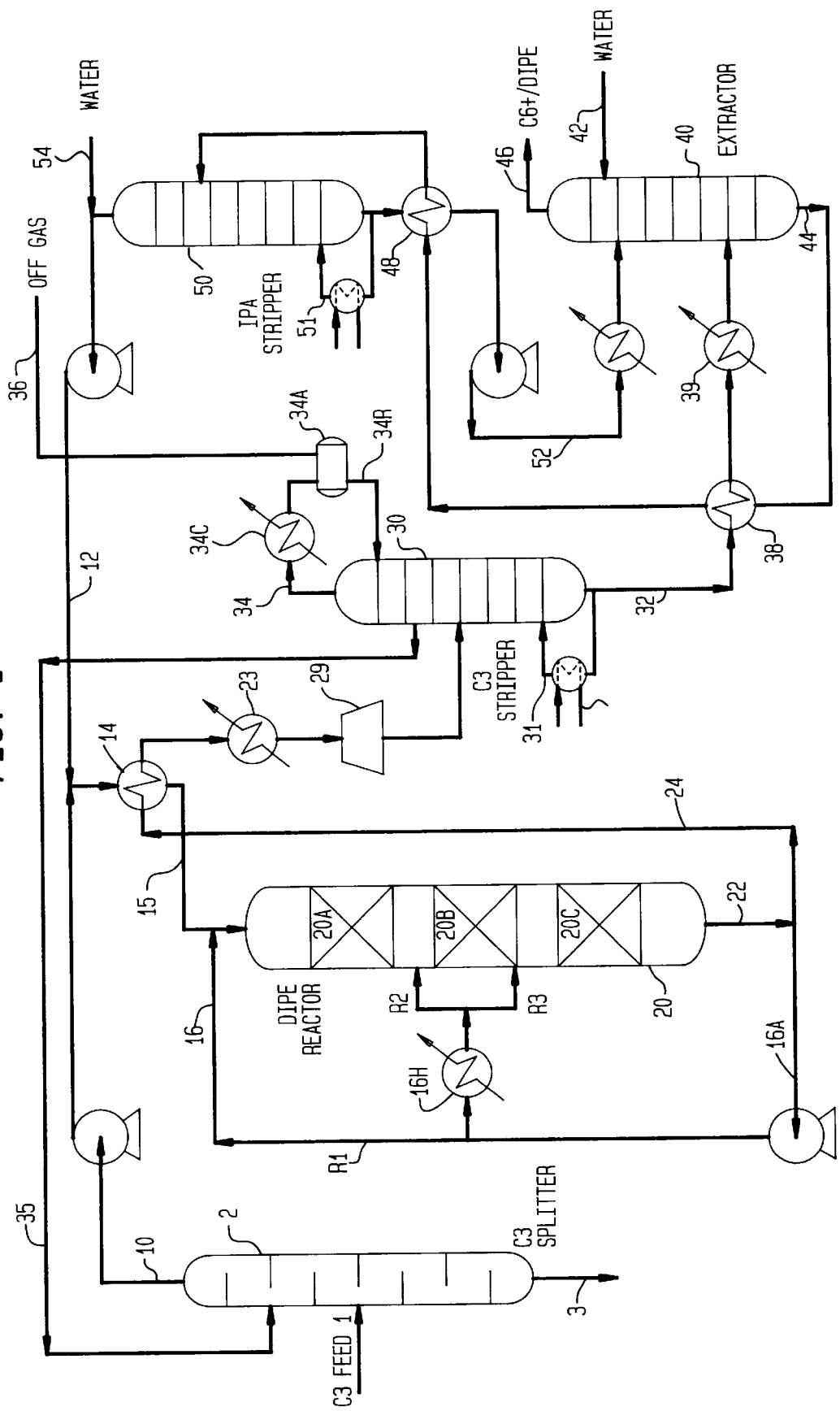
FIG. 1 is a schematic process flow diagram of a first portion of the improved process.

Referring to FIG. 1, a process flow diagram depicts production of diisopropyl ether by hydration of fresh olefinic feedstock stream, which is introduced as a propane-propene mixture via inlet 1 to feed splitter tower 2 to recover a propane-rich bottoms stream 3, which will also contain any $C_4+$ components in the feedstock. An overhead stream consisting essentially of propene ($C_3=$, propylene) is pumped along with water from stream 12 through heat exchanger 14 to bring the reactants and recycle stream 16 to the process conditions for etherification in vertical reactor 20 in contact with porous solid acidic olefin hydration catalyst.

The reactor vessel 20 contains a series of fixed bed adiabatic hydration reaction zones 20A, 20B, 20C maintained under olefin hydration conditions. Static mixers and liquid distributors may b e employed before each bed to promote operation in a single homogeneous phase, as localized high concentrations of water or propene are known to deactivate acidic catalysts (both zeolites and resins). Preferably, at least one hydration reaction zone contains porous zeolite catalyst, such as zeolite Beta.

A fluid handling system is operatively connected for recovering a liquid reactor effluent stream 22 from the last zone 20C. This can be achieved by splitting effluent stream 22 into a liquid product recovery stream 24 and a liquid recycle stream 16A, which is recycled to the multizone reactor 20 as a plurality of flow-controlled recycle streams R3, R2, R3. Heat exchanger 16H cools the interstage quench streams R2, R3 below the process temperature, thus balancing the adiabatic heat of reaction from the preceding zone. Reactor 20 is operated continuously by passing the liquid recycle stream 16A for direct mixing with the reactor feedstream. Reaction temperature can be controlled in zones 20B, 20C by varying the degree of cooling and/or flow rate of the recycle stream in unit 16H. Typically, the reactor effluent and liquid product recovery stream consist essentially of 0.5–10 wt % water, 20–60 wt % propene, 20–30 wt % di-isopropyl ether, 10–15 wt % isopropanol, and various amounts of unreacted light $C_3$— materials, such as 5 to 40 wt % total $C_3$—. Typically, propane and $C_2$— components comprise 0.1–10 wt % and 3–40 wt %, respectively.

The amount of unfractionated liquid recycle stream 16 may be sufficient to maintain a substantially homogeneous single liquid reaction phase in the primary hydration zone 20A under reaction conditions. Use of DIPE, IPA containing product f or quench will also promote single phase operation. The first liquid product stream 24 is passed via exchangers 14, 23 and fluid handling unit 29 to the product fractionation system, as described.

Effluent stream 24 is fractionated in the product recovery system first in $C_3$ stripper column 30, equipped with reboiler means 31, to recover a liquid ether-rich stream 32. The column overhead vapor stream 34 is cooled in condenser means 34C to condense a large portion of $C_3$ and $C_2$ hydrocarbons for recycle via accumulator means 34A and recycle means 34R. Advantageously, a high recycle rate is maintained in the range of 25:1 to 100:1, preferably about 75:1. A propene-rich $C_3$ stream 35 is withdrawn in a upper portion of column 30 for recycle to tower 2 via line 35. Light hydrocarbons may be purged from the system via line 36.

It is advantageous to recover isopropanol for recycle to the reactor to provide isopropanol by-product stream for further conversion to di-isopropyl ether. In the DIPE system depicted, unfractionated liquid recycle stream 16A is passed to reactor 20 at a high rate, usually about four times the total weight of propene and water reactants in the product recovery stream 24; the exact quantity depends on conversion targets, feed properties, etc.

Ether-rich stream 32 containing by-product isopropanol, unreacted propene, water and $C_6+$ hydrocarbon oligomer is further separated after passing through heat exchangers 38, 39 to extractor unit 40, where it is contacted with feed water 42 and/or water recycle stream 52 to extract isopropanol in an aqueous phase 44. A wet product stream 46 consisting essentially of DIPE and by-product $C_6+$ propene oligomer (with small amounts of water and IPA) is recovered from the extraction unit 40, and can be further processed to remove excess water. The extract phase 44 is pass ed via exchangers 38, 48 to IPA stripper column 50 to obtain an overhead isopropanol recycle stream 12. Makeup water stream 54 may be added to the IPA recycle stream 12, as required to maintain the reactor conditions. A portion of the stripper bottom stream is passed through reboiler means 51 and liquid aqueous stream 52 is recycled through the extraction loop via unit 40.

Due to the relatively low equilibrium conversion of propene (~65%), it is desirable to recycle the unconverted propene. However, commercial feed streams contain trace amounts of $C_2$— material, such as ethene, ethane and/or methane, which would accumulate in the recycle loop. Purging of this material results in losses of valuable propene. Allowing the $C_2$— to accumulate before purging results in poor performance of the separation systems. Using lean oil absorbers to remove the $C_2$— material introduces cost, complexity and potential catalyst poisons.

Purification of the fresh feed is ineffective, because trace levels of $C_2$'s or other light components will build up and require purging with subsequent loss of propene. In practice typical of IPA plants, the purged material is sent to a gas plant, however, this is expensive as it involves reprocessing large volumes of propene.

As shown in Tables 1–4, the present invention utilizes a propane/propene (P/P) stripper to concentrate the $C_2$— material prior to purging. As demonstrated in Table 2 a 20% increase in DIPE production is achieved with the present invention, as compared to a simple purge, Table 1. This invention results in a 137% savings in P/P splitter utilities compared to allowing the $C_2$— material to accumulate, Table 3. Table 3 demonstrates the poor performance of the P/P splitter at higher pressure. However, due to the relative volatility differences of DIPE and propene, performing the $C_2$— concentration in the P/P stripper at high pressure does not adversely impact the operation of this column. High pressure also allows for elimination of a recycle pump for stream 35.

Unit Operations for P/P Stripper—Flow rates are given in pound-moles (lb-mols) per hour. Stripper (30) is exemplified for the process flow rates of Table 2 as a vertical column with 22 trays for contact stages, designated 1–22 from top to bottom. Liquid stream 24 (1059.0 lb-mols; 411 psia, 223° F.) from the reactor is fed to tray 15 in a mid portion of the column, and liquid product stream 32 (417.3 lb-mols; 412 psia, 355° F.) is recovered from bottom tray 22. A side draw is made to remove liquid $C_3$ stream 35 (1059.0 lb-mols; 410 psia, 145° F.) from tray 5. Overhead vapor stream 34 (2387.2 lb-mols; 400psia, 103.4° F.) is substantially condensed to provide reflux stream 34R (2356.1 lb-mols) at a molar reflux ratio of 75.7:1 and a $C_2$—rich vapor purge stream 36 (31.1 lb-mols) is removed from the system. The reflux as a molar ratio of liquid feed is 1.56:1.

Improved stripper design with large reflux serves to concentrate both the overhead and sidedraw streams, with placement of the sidedraw in the top 25%–10% of the column contributing to a balancing of concentration of $C_3$ components between recycle and purge streams. Excessive amounts of $C_2$— light gas components in the stripper overhead would require condenser coolant to be less than a standard 100° F. cooling water stream. The side draw stream 35 is passed to the prefractionation P/P splitter unit 2, which can be operated at 1800 kPa (about 265 psia) for significant energy savings.

The stripper purge stream has an optimal $C_2$— light gas 40–70 wt %. At higher light gas content higher pressure and refrigeration are required to condense the overhead stream. At lower light gas content a substantial amount of propylene may be lost to the offgas. Location of the side draw is optimized to allow the singe reflux stream 30 to produce the desired purity for both streams 35 and 36. The use of the stripper to remove light gas components also improves reactor performance by increasing propene purity and phase density, which influence reaction rates favorably.

TABLE 1

Simple Purge Design

| Stream No. | P/P Splitter Feed <1> | $C_3$ Recycle <35> | $C_3$+ off <3> | $C_3^-$ Rich <10> | IPA/ $H_2O$ <I2> | $R_x$ Effluent <24> |
|---|---|---|---|---|---|---|
| lb-mol/hr | | | | | | |
| C2= | 0.7 | 1.3 | 0.0 | 2.0 | 0.0 | 2.0 |
| C2 | 17.6 | 43.2 | 0.0 | 60.8 | 0.0 | 60.8 |
| C3= | 449.7 | 441.1 | 5.7 | 885.2 | 0.0 | 526.7 |
| C3 | 136.4 | 271.3 | 89.9 | 319.2 | 0.0 | 319.2 |
| C4= | 14.7 | 0.0 | 14.7 | 0.0 | 0.0 | 0.0 |
| C6=+ | 0.0 | 0.0 | 0.0 | 0.0 | 0.0 | 22.2 |
| DIPE | 0.0 | 0.0 | 0.0 | 0.0 | 7.1 | 162.0 |
| IPA | 0.0 | 0.0 | 0.0 | 0.0 | 133.9 | 138.3 |
| H2O | 0.0 | 0.1 | 0.0 | 0.0 | 205.5 | 46.3 |
| Total | 619.1 | 757.1 | 110.3 | 1267.2 | 346.5 | 1277.5 |

| Stream No. | $R_x$ Recycle <16A> | $C_2$ Purge <36> | Bottoms <32> | DIPE Raffinate <46> | Water Feed <44> | Stripper Bottoms <52> |
|---|---|---|---|---|---|---|
| C2= | 8.0 | 0.7 | 0.0 | 0.0 | 0.0 | 0.0 |
| C2 | 243.2 | 17.6 | 0.0 | 0.0 | 0.0 | 0.0 |
| C3= | 2106.8 | 85.2 | 0.4 | 0.4 | 0.0 | 0.0 |
| C3 | 1276.8 | 47.5 | 0.4 | 0.4 | 0.0 | 0.0 |
| C4= | 0.0 | 0.0 | 0.0 | 0.0 | 0.0 | 0.0 |
| C6=+ | 88.8 | 0.0 | 22.2 | 22.2 | 0.0 | 0.0 |
| DIPE | 648.0 | 0.0 | 162.0 | 154.9 | 7.1 | 0.0 |
| IPA | 553.0 | 0.0 | 138.3 | 5.1 | 133.6 | 0.4 |
| H2O | 185.2 | 0.0 | 46.2 | 4.8 | 1364.6 | 1222.9 |
| Total | 5110.0 | 150.9 | 369.5 | 187.9 | 1505.3 | 1223.3 |

TABLE 1-continued

Simple Purge Design

| Stream No. | Water Feed <42> | Water Feed <54> | $H_2O$ Off <66> | DIPE Product <54> | Purge <62> |
|---|---|---|---|---|---|
| C2= | 0.0 | 0.0 | 0.0 | 0.0 | 0.0 |
| C2 | 0.0 | 0.0 | 0.0 | 0.0 | 0.0 |
| C3= | 0.0 | 0.0 | 0.0 | 0.0 | 0.4 |
| C3 | 0.0 | 0.0 | 0.0 | 0.0 | 0.4 |
| C4= | 0.0 | 0.0 | 0.0 | 0.0 | 0.0 |
| C6=+ | 0.0 | 0.0 | 0.0 | 22.1 | 0.0 |
| DIPE | 0.0 | 0.0 | 0.0 | 154.4 | 0.5 |
| IPA | 0.0 | 0.0 | 0.0 | 5.1 | 0.0 |
| H2O | 100.8 | 63.4 | 4.0 | 0.7 | 0.1 |
| Total | 100.8 | 63.4 | 4.0 | 182.3 | 1.4 |

TABLE 2

Improved Process Design

| Stream No. | P/P Splitter Feed <1> | $C_3$ Recycle <35> | $C_3$+ Off <3> | $C_3^-$ Rich <10> | IPA/ $H_2O$ <I2> | $R_x$ Effluent <24> |
|---|---|---|---|---|---|---|
| lb-mol/hr | | | | | | |
| C2= | 0.7 | 0.6 | 0.0 | 1.3 | 0.0 | 1.3 |
| C2 | 17.6 | 43.2 | 0.0 | 60.8 | 0.0 | 60.8 |
| C3= | 449.7 | 625.2 | 7.9 | 1067.1 | 0.0 | 634.9 |
| C3 | 136.4 | 389.9 | 132.1 | 394.1 | 0.0 | 394.1 |
| C4= | 14.7 | 0.0 | 14.8 | 0.0 | 0.0 | 0.0 |
| C6=+ | 0.0 | 0.0 | 0.0 | 0.0 | 0.0 | 26.7 |
| DIPE | 0.0 | 0.0 | 0.0 | 0.0 | 5.7 | 192.4 |
| IPA | 0.0 | 0.0 | 0.0 | 0.0 | 136.0 | 141.4 |
| H2O | 0.0 | 0.1 | 0.0 | 0.0 | 247.9 | 56.0 |
| Total | 619.1 | 1059.0 | 154.8 | 1523.3 | 389.6 | 1507.5 |

| Stream No. | $R_x$ Recycle <16A> | $C_2$ Purge <36> | Bottoms <32> | DIPE Raffinate <46> | Water Feed <44> | Stripper Bottoms <52> |
|---|---|---|---|---|---|---|
| C2= | 5.2 | 0.7 | 0.0 | 0.0 | 0.0 | 0.0 |
| C2 | 243.2 | 17.6 | 0.0 | 0.0 | 0.0 | 0.0 |
| C3= | 2539.6 | 9.1 | 0.6 | 0.6 | 0.0 | 0.0 |
| C3 | 1576.4 | 3.7 | 0.4 | 0.4 | 0.0 | 0.0 |
| C4= | 0.0 | 0.0 | 0.0 | 0.0 | 0.0 | 0.0 |
| C6=+ | 106.8 | 0.0 | 26.7 | 26.7 | 0.0 | 0.0 |
| DIPE | 769.6 | 0.0 | 192.4 | 186.8 | 5.6 | 0.0 |
| IPA | 565.6 | 0.0 | 141.4 | 6.2 | 135.6 | 0.5 |
| H2O | 224.0 | 0.0 | 55.8 | 5.8 | 1656.4 | 1498.9 |
| Total | 6030.0 | 31.1 | 417.3 | 226.6 | 1797.6 | 1499.4 |

| Stream No. | Water Feed <42> | Water Feed <54> | $H_2O$ Off <66> | DIPE Product <54> | Purge <62> |
|---|---|---|---|---|---|
| C2= | 0.0 | 0.0 | 0.0 | 0.0 | 0.0 |
| C2 | 0.0 | 0.0 | 0.0 | 0.0 | 0.0 |
| C3= | 0.0 | 0.0 | 0.0 | 0.0 | 0.6 |
| C3 | 0.0 | 0.0 | 0.0 | 0.0 | 0.4 |
| C4= | 0.0 | 0.0 | 0.0 | 0.0 | 0.0 |
| C6=+ | 0.0 | 0.0 | 0.0 | 26.6 | 0.1 |
| DIPE | 0.0 | 0.0 | 0.0 | 186.2 | 0.6 |
| IPA | 0.0 | 0.0 | 0.1 | 6.1 | 0.0 |
| H2O | 107.8 | 90.1 | 4.8 | 0.9 | 0.1 |
| Total | 107.8 | 90.1 | 4.9 | 219.9 | 1.8 |

TABLE 3

Accumulate C2's Prior to Purge

| Stream No. | P/P Splitter Feed <1> | C₃ Recycle <35> | C₃+ off <3> | C₃⁻ Rich <10> | IPA/ H₂O <12> | Rₓ Effluent <24> |
|---|---|---|---|---|---|---|
| lb-mol/hr | | | | | | |
| C2= | 0.7 | 8.1 | 0.0 | 8.8 | 0.0 | 8.8 |
| C2 | 17.6 | 263.2 | 0.0 | 280.8 | 0.0 | 280.8 |
| C3= | 449.7 | 609.2 | 1.6 | 1057.1 | 0.0 | 629.0 |
| C3 | 136.4 | 228.4 | 127.8 | 235.2 | 0.0 | 235.3 |
| C4= | 14.7 | 0.0 | 14.8 | 0.0 | 0.0 | 0.0 |
| C6=+ | 0.0 | 0.0 | 0.0 | 0.0 | 0.0 | 26.5 |
| DIPE | 0.0 | 0.0 | 0.0 | 0.0 | 5.6 | 190.6 |
| IPA | 0.0 | 0.0 | 0.0 | 0.0 | 134.5 | 139.7 |
| H2O | 0.0 | 0.1 | 0.0 | 0.0 | 247.0 | 56.8 |
| Total | 619.1 | 1109.0 | 144.2 | 1581.9 | 387.1 | 1567.4 |

| Stream No. | Rₓ Recycle <16A> | C₂ Purge <36> | Bottoms <32> | DIPE Raffinate <46> | Water Feed <44> | Stripper Bottoms <52> |
|---|---|---|---|---|---|---|
| C2= | 35.2 | 0.7 | 0.0 | 0.0 | 0.0 | 0.0 |
| C2 | 1123.2 | 17.6 | 0.0 | 0.0 | 0.0 | 0.0 |
| C3= | 2516.0 | 19.2 | 0.6 | 0.6 | 0.0 | 0.0 |
| C3 | 941.2 | 6.5 | 0.3 | 0.3 | 0.0 | 0.0 |
| C4= | 0.0 | 0.0 | 0.0 | 0.0 | 0.0 | 0.0 |
| C6=+ | 106.0 | 0.0 | 26.5 | 26.5 | 0.0 | 0.0 |
| DIPE | 762.4 | 0.0 | 190.6 | 185.0 | 5.5 | 0.0 |
| IPA | 558.8 | 0.0 | 139.7 | 6.0 | 134.1 | 0.5 |
| H2O | 227.2 | 0.0 | 56.7 | 5.8 | 1639.3 | 1487.2 |
| Total | 6269.6 | 44.0 | 414.4 | 224.2 | 1778.9 | 1487.7 |

| Stream No. | Water Feed <42> | Water Feed <54> | H₂O Off <66> | DIPE Product <54> | Purge <62> |
|---|---|---|---|---|---|
| C2= | 0.0 | 0.0 | 0.0 | 0.0 | 0.0 |
| C2 | 0.0 | 0.0 | 0.0 | 0.0 | 0.0 |
| C3= | 0.0 | 0.0 | 0.0 | 0.0 | 0.6 |
| C3 | 0.0 | 0.0 | 0.0 | 0..0 | 0.3 |
| C4= | 0.0 | 0.0 | 0.0 | 0.0 | 0.0 |
| C6=+ | 0.0 | 0.0 | 0.0 | 26.4 | 0.0 |
| DIPE | 0.0 | 0.0 | 0.0 | 184.6 | 0.5 |
| IPA | 0.0 | 0.0 | 0.1 | 6.0 | 0.0 |
| H2O | 101.6 | 94.4 | 4.8 | 0.9 | 0.1 |
| Total | 101.6 | 94.4 | 4.9 | 217.9 | 1.5 |

TABLE 4

Comparison of Column Performance

| Column | P/P Splitter | P/P Stripper | IPA Stripper | DIPE Dryer |
|---|---|---|---|---|
| Table 4A - Simple purge | | | | |
| Oper pressure, psi | 266.0 | 302.0 | 40.0 | 30.0 |
| Diameter, feet | 6.5 | 4.5 | 2.5 | 2.5 |
| Theoretical Stages | 66.0 | 22.0 | 8.0 | 8.0 |
| Cond Temp, °F. | 102.0 | 103.0 | — | 120.0 |
| Cond Duty, MMBTU/hr | 15.2 | 10.9 | — | -0.5 |
| Reboil Temp, °F. | 134.0 | 317.0 | 268.0 | 197.0 |
| Reboil Duty, MMBTU/hr | 15.3 | 12.7 | 6.1 | 1.5 |
| Reflux Ratio, wt/wt | 1.2 | 1.4 | 0 | 0.8 |
| Table 4B - Improved Process Design | | | | |
| Oper pressure, psi | 266.0 | 412.0 | 40.0 | 30.0 |
| Diameter, feet | 6.5 | 4.5 | 2.5 | 2.5 |
| Theoretical Stages | 66.0 | 22.0 | 8.0 | 8.0 |
| Cond Temp, °F. | 103.0 | 103.0 | — | 120.0 |
| Cond Duty, MMBTU/hr | 22.0 | 9.1 | — | -0.6 |
| Reboil Temp, °F. | 132.0 | 355.0 | 268.0 | 197.0 |
| Reboil Duty, MMBTU/hr | 20.9 | 12.5 | 5.9 | 1.8 |
| Reflux Ratio, wt/wt | 1.6 | 75.7 | 0 | 0.8 |
| Table 4C - Accumulate C2's | | | | |
| Oper pressure, psi | 326.0 | 357.0 | 40.0 | 30.0 |
| Diameter, feet | 11.5 | 4.5 | 2.5 | 2.5 |
| Theoretical Stages | 66.0 | 22.0 | 8.0 | 8.0 |
| Cond Temp, °F. | 101.0 | 101.0 | — | 120.0 |
| Cond Duty, MMBTU/hr | 49.3 | 10.5 | — | -0.6 |
| Reboil Temp, °F. | 151.0 | 339.0 | 268.0 | 197.0 |
| Reboil Duty, MMBTU/hr | 49.5 | 11.9 | 6.1 | 1.8 |
| Reflux Rati0, wt/wt | 5.0 | 1.0 | 0 | 0.8 |

The unique nature of the improved DIPE reactor and product recovery system allows the two significantly different separations, $C_2/C_3$ and $C_3$/DIPE, to be performed in the same column with a single reflux, and also allows the DIPE unit to obtain high propene utilization while processing feeds containing appreciable amounts of $C_2$— impurities, i.e., 0.1 to 10 wt %.

Limitations on water miscibility, performance, blended gasoline product vapor pressure (RVP), and corrosion make the ether the preferred fuel blending component for oxygenate and octane requirements over the alcohol. Due to the relatively high IPA content in the DIPE azeotrope, extraction is the preferred method of meeting limitations on alcohol content (typically 2%) for pipeline transport. Location of the water makeup and operation of the IPA stripper is important to balance IPA production with IPA losses from the system while maintaining single phase operation.

The DIPE product stream 46 from the extractor 40 is saturated with ~0.3–0.7 wt % water which would (depending on IPA content) lead to haze formation in gasoline at low temperatures. The presence of >3% oligomeric material in the fuel grade DIPE introduces uncertainty as to whether conventional drying methods will be effective.

Figure 2:
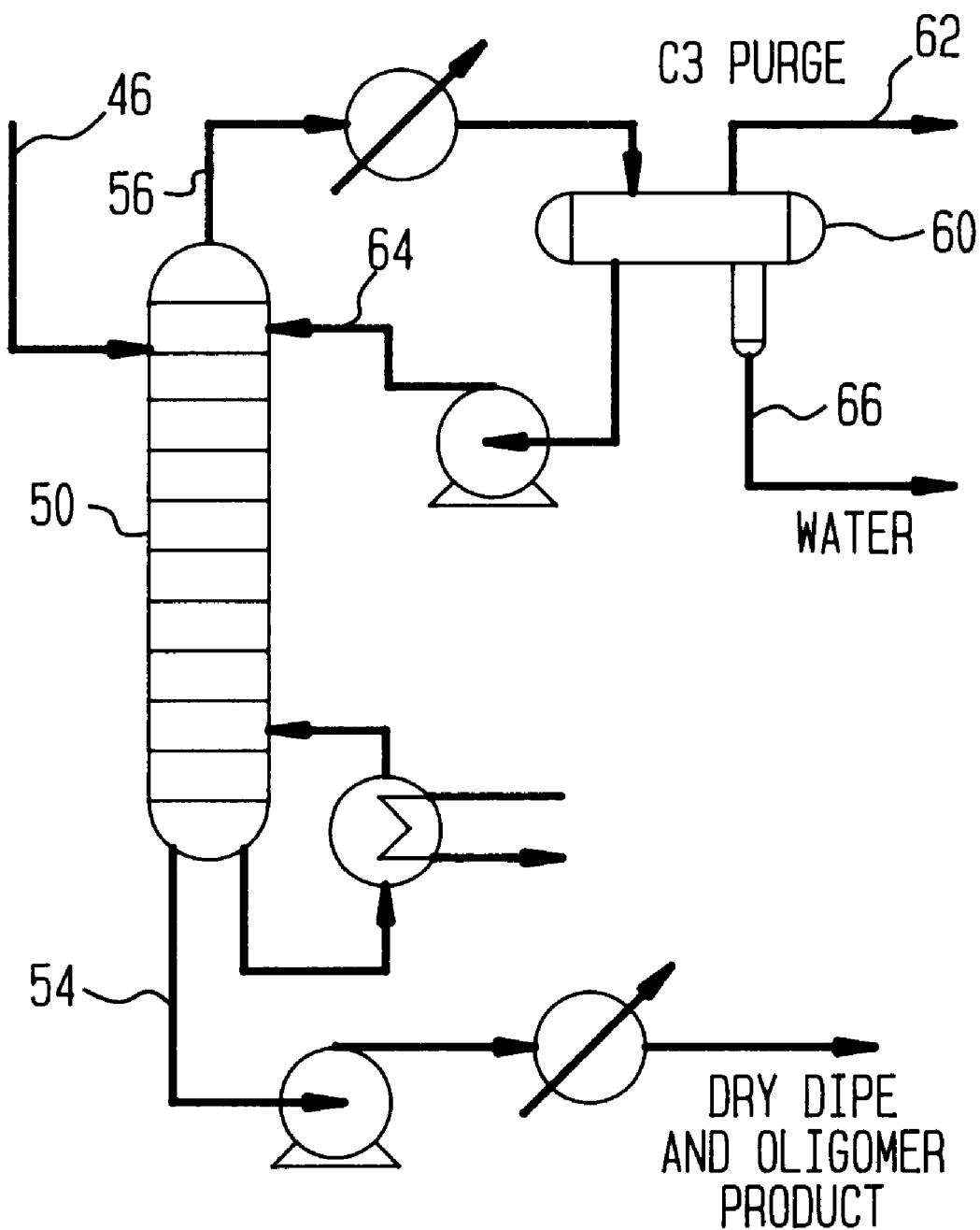
FIG. 2 is a schematic flow diagram of a second portion of the process, showing relationship of a product drying section to the first process portion.

In FIG. 2, the wet DIPE product containing $C_6$ oligomer is introduced via an upper stage portion of vertical distillation tower 50, which is equipped with conventional tower bottoms reboiler heating means 52 and outlet means 54 for withdrawing dry DIPE product. The vapor overhead is withdrawn via overhead conduit 56, cooled in heat exchanger 58 and passed to phase separator means 60. The uncondensed vapor stream 62 purges $C_3$'s from the system, and a condensed liquid stream 64 is returned to a top stage of tower 50 as reflux. The preferred reflux ratio is about 2:1 to 40:1, depending on the IPA and water content. Water is removed via line 66, and may be recycled to other unit operations.

Figure 3:
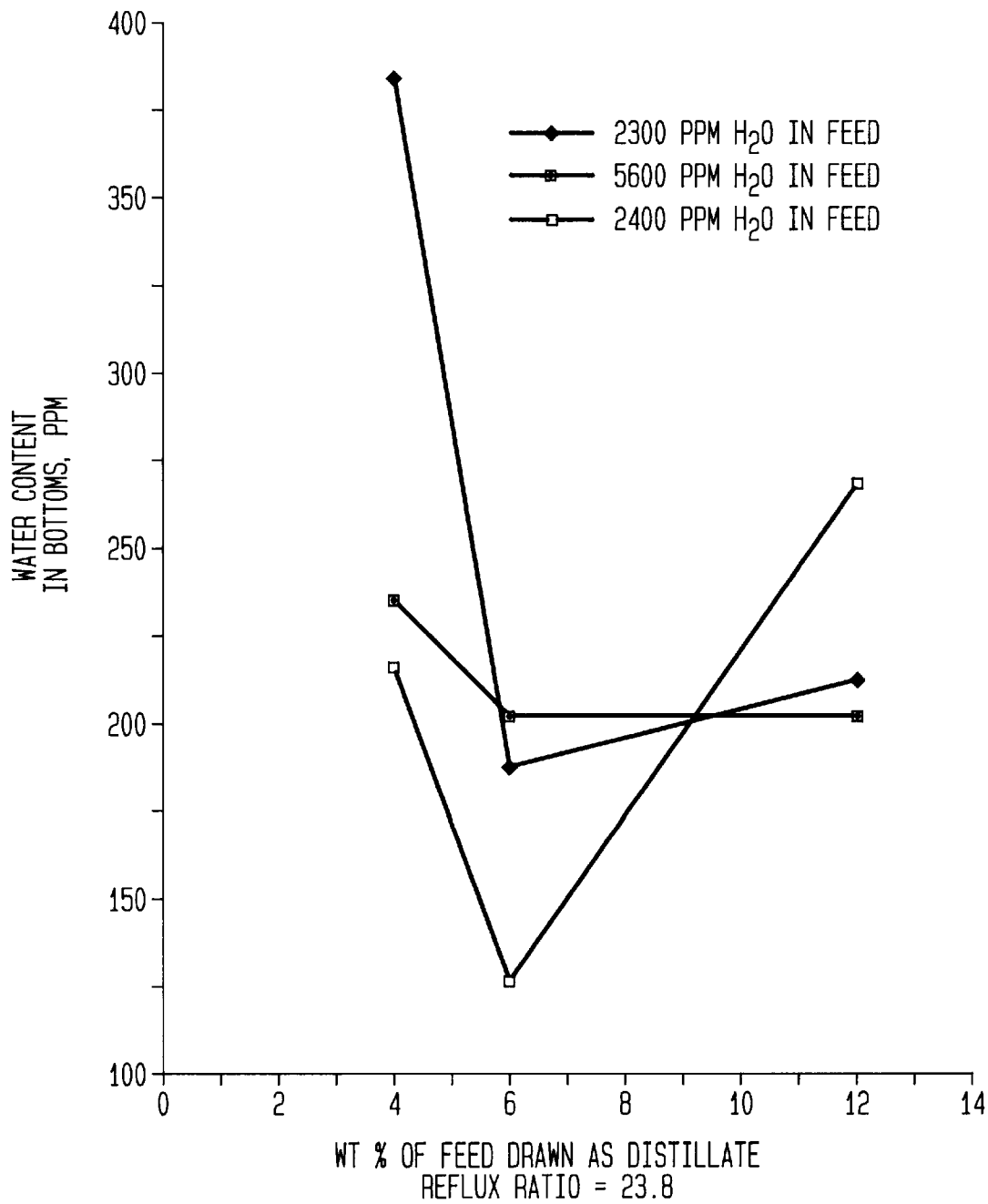
FIG. 3 is a graphic plot of dry product water content for wet product stream compositions.

The effectiveness of drying crude DIPE via distillation is shown in FIG. 3 and Table 5 for three different levels of DIPE purity; high purity (~7% oligomer), medium purity (~13% oligomer) and low purity (~23% oligomer). FIG. 3 shows semi-batch distillation water content for the dry product (bottoms) versus the weight percent feed drawn as distillate. The drying is very effective as low levels of distillate draw produce very dry DIPE (~0.03 wt % water) for all grades of DIPE. Semi-batch experiments were performed as they produce more information on the phase behavior as a function of composition.

As shown in FIG. 3 and Table 5, it has been found that the presence of the oligomer has little effect on the efficiency of water removal by distillation. This is surprising considering the complex interactions of the molecules in the azeotrope essential for effective drying.

Chemical grade DIPE (<0.5% oligomer) is dried via distillation utilizing the DIPE-IPA-$H_2O$ interactions which form a minimum boiling heterogeneous azeotrope rich in water. Upon condensing, the overhead phase separates and a heavy water phase is decanted. However, $C_6=-C_9=$ oligomers do not form an azeotrope with water. Thus it is expected that drying DIPE containing large amounts of oligomer whose boiling range (128° F.–300° F.) brackets that of the DIPE azeotrope via distillation would not be effective. However, as shown in FIG. 3, drying via distillation is effective for the low purity DIPE.

By comparison, experiments have verified that drying via sorption on 3A molecular sieves can achieve water separation to provide DIPE product containing <0.1 wt % (1000 ppm) water.

TABLE 5

| | DIPE Drying | | |
|---|---|---|---|
| | High Purity | Medium Purity | Low Purity |
| Wt % | | | |
| DIPE | 90.34 | 81.84 | 74.50 |
| IPA | 2.42 | 5.10 | 2.17 |
| C9= | 3.38 | 7.50 | 16.10 |
| C6= | 3.62 | 5.00 | 7.02 |
| $H_2O$ | 0.24 | 0.56 | 0.23 |
| | (2400 ppm) | (5600 ppm) | (2300 ppm) |

The DIPE product from the extractor is saturated with ~0.3–0.7 wt % water which would lead to haze formation at low temperatures in gasoline. Thus, dry product recovery becomes an important unit operation in the overall DIPE production system. The presence of >3% oligomeric material in the fuel grade DIPE introduces uncertainty as to whether conventional drying methods will be effective. The improved process provides a DIPE product stream containing less than 0.1 weight percent (wt %) water, preferably about 100–400 ppm (parts per million by weight).

It is believed that the improved drying technique is effective because the hydrocarbon molecules do not have a tendency to hydrogen-bond with the water molecules. This is the reason why low concentrations of water in hydrocarbons typically exit in the overhead stream below the normal boiling point of water. However, it is surprising that in the DIPE environment, where strong interactions between water-DIPE-IPA occur, that this phenomenon also occurs.

As shown in FIG. 4 and Table 5, the presence of the oligomer has little effect on the efficiency of drying via distillation. This is surprising considering the complex interactions of the molecules in the azeotrope are essential for effective drying. In addition, experiments have verified that drying via sorption on 3A molecular sieves achieved the water separation (<0.1 wt %).

While the invention has been described by specific examples and embodiments, there is no intent to limit the inventive concept except as set forth in the following claims.

We claim:

1. In the process for the production of diisopropyl ether by hydration and etherification of hydrocarbon feedstock containing propene, propane and $C_2$— light gas components, which comprises contacting the feedstock and water in a catalytic reactor containing porous solid acidic olefin hydration catalyst under olefin hydration and etherification conditions, the improvement which comprises:

recovering a liquid effluent stream from said catalytic reactor containing diisopropyl ether, isopropanol, water, unreacted propene, hydrocarbon oligomer by-product, propane and $C_2$— light gas components;

separating said liquid effluent stream in a vertical stripper column having a lower reboiler portion and an upper contact portion;

recovering an overhead vapor stream containing propene, propane and $C_2$— light gas components from the stripper column;

cooling the overhead vapor stream to provide a condensed reflux stream rich in propene and propane;

removing the $C_2$— light gas components from the condensed reflux stream;

recycling the reflux stream to the upper contact portion of the stripper column;

recovering a predominantly $C_3$ recycle stream from the upper contact portion of the stripper column for recycle to the catalytic reactor;

recovering from the stripper column an ether-rich liquid stream containing said oligomer and isopropanol;

extracting the ether-rich liquid stream with water to remove isopropanols in an aqueous extract stream and recover a wet liquid product raffinate stream consisting essentially of di-isopropyl ether, oligomer and at least 0.2 wt % water;

distilling said wet liquid product stream to recover a major amount of water from the wet liquid product stream along with residual $C_3$ hydrocarbons and to recover a dry bottom ether product stream containing less than 0.1 wt % water and at least 3 wt % oligomer.

2. The process of claim 1 including the step of splitting a first liquid effluent stream into a liquid product recovery stream and a liquid recycle stream;

cooling at least a portion of said liquid recycle stream: and passing said cooled liquid recycled stream as interstage quench between serial fixed bed hydration zones in said catalytic reactor for controlling reaction temperature, wherein total liquid recycle is combined with fresh feed at a weight ratio of 2:1 to 10:1 recycle:feed.

3. The process of claim 1 wherein said solid catalyst comprises zeolite Beta, and wherein the hydration zone conditions comprise temperature of 100 to 250° C.

4. A process for production of diisopropyl ether by conversion of hydrocarbon feedstock containing propene, propane and $C_2$— light gas components, comprising the steps of:

prefractionating fresh feedstock containing propene, propane and $C_2$— light gas components to provide a reactor feedstream rich in propene;

contacting the feedstream and water in a catalytic reactor with acidic catalyst under olefin hydration and etherification reaction conditions, wherein the catalyst comprises porous zeolite having a pore size of 5–8 Angstroms, and reaction temperature is maintained at 100 to 250° C.;

recovering from the catalytic reactor a liquid reactor effluent stream containing 0.5–10 wt % water, 20–60 wt % propene, 20–30 wt % di-isopropyl ether, 10–15 wt % isopropanol, at least 5 wt % total propane, 0 to 20 wt % oligomer, and 0.1 to 10 wt % $C_2$— components;

splitting the liquid reactor effluent stream into a liquid product recovery stream and a liquid recycle stream;

passing the liquid product recovery stream to a vertical stripper column having a lower reboiler portion and an upper contact portion for separation into a $C_2$— light gas stream, a liquid stream rich in propene and propane and an ether-rich liquid stream containing said oligomer and isopropanol;

recycling said liquid stream rich in propene and propane to said prefractionating step;

extracting the ether-rich liquid stream with water to remove isopropanol-rich aqueous extract and recover a wet liquid product stream consisting essentially of di-isopropyl ether, oligomer and at least 0.2 wt % water;

distilling said wet liquid product stream to recover a major amount of water from the wet liquid product stream along with residual $C_3$ hydrocarbons and to recover a dry bottom ether product stream containing less than 0.1 wt % water and at least 3 wt % oligomer.

* * * * *